US006914046B1

(12) United States Patent
Hirsch et al.

(10) Patent No.: US 6,914,046 B1
(45) Date of Patent: Jul. 5, 2005

(54) NF-κB ACTIVATION INHIBITORS, AND THEIR PHARMACEUTICAL USES

(75) Inventors: Francois Hirsch, Arcueil (FR); Astrid Haeffner, Meudon la Foret (FR)

(73) Assignee: Centre National de la Recherche Scientifique, Paris Cedex (FR)

(*) Notice: Subject to any disclaimer, the term of this patent is extended or adjusted under 35 U.S.C. 154(b) by 0 days.

(21) Appl. No.: 09/856,796

(22) PCT Filed: Nov. 24, 1999

(86) PCT No.: PCT/FR99/02897

§ 371 (c)(1),
(2), (4) Date: Sep. 7, 2001

(87) PCT Pub. No.: WO00/30587

PCT Pub. Date: Jun. 2, 2000

(30) Foreign Application Priority Data

Nov. 24, 1999 (FR) .............................. 98 14858

(51) Int. Cl.[7] ..................... C07K 14/61; A61K 38/00
(52) U.S. Cl. ..................... 514/12; 514/2; 514/34; 514/806; 536/6.4; 424/184.1
(58) Field of Search .................. 514/12, 2, 34, 514/806, 43; 536/6.4; 435/6

(56) References Cited

U.S. PATENT DOCUMENTS 5,725,851 A * 3/1998 Wong et al. ................ 424/85.2
2002/0068690 A1 * 6/2002 Baldwin et al. ................ 514/1

FOREIGN PATENT DOCUMENTS

WO        WO 99/06040        2/1999

OTHER PUBLICATIONS

Singh et al., Journal of Immunology, 1996, vol. 157, No. 10, pp. 4412–4420.*

M.Digicaylioglu et al., Neuroprotection From Nitric Oxide by Erythropoietin (EPO) is Mediated by NFKappaB, *Society for Neuroscience*, Part 2, Los Angeles, CA, Nov. 7012, 1998.

A.Haeffner et al, Inhibitory Effect of Growth Hormone on TNF–alpha Secretion and Nuclear Factor –kappaB Translocation in Lipopolysaccharide–Stimulated Human Monocytes, *Journal of Immunology*, Feb. 1, 1997, vol. 3, No. 1, pp 1310–1314.

C.Y.Wang et al., TNF– and Cancer Therapy–Induced Apoptosis: Potentiation by Inhibition of NF–kappaB, *Science*, vol. 274, No. 5288, Nov. 1, 1996, pp 784–787.

A.Haeffner et al., Growth Hormone Prevents Human Monocyte Cell From FAS–Mediated Apoptosis by Up–Regulating Bcl–2 Expression, *European Journal of Immunology*, vol. 29, No. 1, Jan. 1999, pp 334–44.

* cited by examiner

Primary Examiner—Gary Nickol
Assistant Examiner—Brandon Fetterolf
(74) Attorney, Agent, or Firm—Young & Thompson (57) ABSTRACT

Compounds inhibiting the activation of the nuclear factor κB (NF-κB) are used for the preparation of medications adapted for the treatment of malignant hemopathies and solid tumors, and for the prevention of the appearance or the treatment, of phenomena of resistance to cytotoxic molecules used in the scope of treatment of the above pathologies, appearing in patients treated with these molecules when the latter are adapted to activate NF-κB.

6 Claims, 6 Drawing Sheets

Experiment 1

Experiment 2

SEQUENCE LISTING

<160> NUMBER OF SEQ ID NOS: 4

<210> SEQ ID NO 1
<211> LENGTH: 609
<212> TYPE: DNA
<213> ORGANISM: Homo sapiens
<220> FEATURE:
<221> NAME/KEY: CDS
<222> LOCATION: (1)..(606)

<400> SEQUENCE: 1

| | | | | | | | | | | | | | | | | |
|---|---|---|---|---|---|---|---|---|---|---|---|---|---|---|---|---|
| atg | gct | aca | ggc | tcc | cgg | acg | tcc | ctg | ctc | ctg | gct | ttt | ggc | ctg | ctc | 48 |
| Met | Ala | Thr | Gly | Ser | Arg | Thr | Ser | Leu | Leu | Leu | Ala | Phe | Gly | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgc | ctg | ccc | tgg | ctt | caa | gag | ggc | agt | gcc | ttc | cca | acc | att | ccc | tta | 96 |
| Cys | Leu | Pro | Trp | Leu | Gln | Glu | Gly | Ser | Ala | Phe | Pro | Thr | Ile | Pro | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| tcc | agg | ctt | ttt | gac | aac | gct | agt | ctc | cgc | gcc | cat | cgt | ctg | cac | cag | 144 |
| Ser | Arg | Leu | Phe | Asp | Asn | Ala | Ser | Leu | Arg | Ala | His | Arg | Leu | His | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| ctg | gcc | ttt | gac | acc | tac | cag | gag | ttt | aac | ccc | cag | acc | tcc | ctc | tgt | 192 |
| Leu | Ala | Phe | Asp | Thr | Tyr | Gln | Glu | Phe | Asn | Pro | Gln | Thr | Ser | Leu | Cys | |
| | 50 | | | | | 55 | | | | | 60 | | | | | |

| | | | | | | | | | | | | | | | | |
|---|---|---|---|---|---|---|---|---|---|---|---|---|---|---|---|---|
| ttc | tca | gag | tct | att | ccg | aca | ccc | tcc | aac | agg | gag | gaa | aca | caa | cag | 240 |
| Phe | Ser | Glu | Ser | Ile | Pro | Thr | Pro | Ser | Asn | Arg | Glu | Glu | Thr | Gln | Gln | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aaa | tcc | aac | cta | gag | ctg | ctc | cgc | atc | tcc | ctg | ctc | atc | cag | tcg | | 288 |
| Lys | Ser | Asn | Leu | Glu | Leu | Leu | Arg | Ile | Ser | Leu | Leu | Leu | Ile | Gln | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| tgg | ctg | gag | ccc | gtg | cag | ttc | ctc | agg | agt | gtc | ttc | gcc | aac | agc | ctg | 336 |
| Trp | Leu | Glu | Pro | Val | Gln | Phe | Leu | Arg | Ser | Val | Phe | Ala | Asn | Ser | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| gtg | tac | ggc | gcc | tct | gac | agc | aac | gtc | tat | gac | ctc | cta | aag | gac | cta | 384 |
| Val | Tyr | Gly | Ala | Ser | Asp | Ser | Asn | Val | Tyr | Asp | Leu | Leu | Lys | Asp | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| gag | gaa | ggc | atc | caa | acg | ctg | atg | ggg | agg | ctg | gaa | gat | ggc | agc | ccc | 432 |
| Glu | Glu | Gly | Ile | Gln | Thr | Leu | Met | Gly | Arg | Leu | Glu | Asp | Gly | Ser | Pro | |
| | 130 | | | | | 135 | | | | | 140 | | | | | |

| | | | | | | | | | | | | | | | | |
|---|---|---|---|---|---|---|---|---|---|---|---|---|---|---|---|---|
| cgg | act | ggg | cag | atc | ttc | aag | cag | acc | tac | agc | aag | ttc | gac | aca | aac | 480 |
| Arg | Thr | Gly | Gln | Ile | Phe | Lys | Gln | Thr | Tyr | Ser | Lys | Phe | Asp | Thr | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tca | cac | aac | gat | gac | gca | cta | ctc | aag | aac | tac | ggg | ctg | ctc | tac | tgc | 528 |
| Ser | His | Asn | Asp | Asp | Ala | Leu | Leu | Lys | Asn | Tyr | Gly | Leu | Leu | Tyr | Cys | |
| | | | 165 | | | | | 170 | | | | | 175 | | | |

| | | | | | | | | | | | | | | | | |
|---|---|---|---|---|---|---|---|---|---|---|---|---|---|---|---|---|
| ttc | agg | aag | gac | atg | gac | aag | gtc | gag | aca | ttc | ctg | cgc | atc | gtg | cag | 576 |
| Phe | Arg | Lys | Asp | Met | Asp | Lys | Val | Glu | Thr | Phe | Leu | Arg | Ile | Val | Gln | |
| | | 180 | | | | | 185 | | | | | 190 | | | | |

| | | | | | | | | | | |
|---|---|---|---|---|---|---|---|---|---|---|
| tgc | cgc | tct | gtg | gag | ggc | agc | tgt | ggc | ttc | tag | 609 |
| Cys | Arg | Ser | Val | Glu | Gly | Ser | Cys | Gly | Phe | | |
| | 195 | | | | | 200 | | | | | |

<210> SEQ ID NO 2
<211> LENGTH: 202
<212> TYPE: PRT
<213> ORGANISM: Homo sapiens

<400> SEQUENCE: 2

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu

-continued

```
                        20                  25                  30
Ser Arg Leu Phe Asp Asn Ala Ser Leu Arg Ala His Arg Leu His Gln
         35                  40                  45
Leu Ala Phe Asp Thr Tyr Gln Glu Phe Asn Pro Gln Thr Ser Leu Cys
 50                  55                  60
Phe Ser Glu Ser Ile Pro Thr Pro Ser Asn Arg Glu Glu Thr Gln Gln
 65                  70                  75                  80
Lys Ser Asn Leu Glu Leu Leu Arg Ile Ser Leu Leu Leu Ile Gln Ser
                 85                  90                  95
Trp Leu Glu Pro Val Gln Phe Leu Arg Ser Val Phe Ala Asn Ser Leu
             100                 105                 110
Val Tyr Gly Ala Ser Asp Ser Asn Val Tyr Asp Leu Leu Lys Asp Leu
         115                 120                 125
Glu Glu Gly Ile Gln Thr Leu Met Gly Arg Leu Glu Asp Gly Ser Pro
     130                 135                 140
Arg Thr Gly Gln Ile Phe Lys Gln Thr Tyr Ser Lys Phe Asp Thr Asn
145                 150                 155                 160
Ser His Asn Asp Asp Ala Leu Leu Lys Asn Tyr Gly Leu Leu Tyr Cys
                 165                 170                 175
Phe Arg Lys Asp Met Asp Lys Val Glu Thr Phe Leu Arg Ile Val Gln
             180                 185                 190
Cys Arg Ser Val Glu Gly Ser Cys Gly Phe
         195                 200
```

<210> SEQ ID NO 3
<211> LENGTH: 582
<212> TYPE: DNA
<213> ORGANISM: Homo sapiens
<220> FEATURE:
<221> NAME/KEY: CDS
<222> LOCATION: (1)..(579)

<400> SEQUENCE: 3

```
atg ggg gtg cac gaa tgt cct gcc tgg ctg tgg ctt ctc ctg tcc ctg      48
Met Gly Val His Glu Cys Pro Ala Trp Leu Trp Leu Leu Leu Ser Leu
 1               5                  10                  15 ctg tcg ctc cct ctg ggc ctc cca gtc ctg ggc gcc cca cca cgc ctc      96
Leu Ser Leu Pro Leu Gly Leu Pro Val Leu Gly Ala Pro Pro Arg Leu
             20                  25                  30 atc tgt gac agc cga gtc ctg gag agg tac ctc ttg gag gcc aag gag     144
Ile Cys Asp Ser Arg Val Leu Glu Arg Tyr Leu Leu Glu Ala Lys Glu
         35                  40                  45 gcc gag aat atc acg acg ggc tgt gct gaa cac tgc agc ttg aat gag     192
Ala Glu Asn Ile Thr Thr Gly Cys Ala Glu His Cys Ser Leu Asn Glu
 50                  55                  60 aat atc act gtc cca gac acc aaa gtt aat ttc tat gcc tgg aag agg     240
Asn Ile Thr Val Pro Asp Thr Lys Val Asn Phe Tyr Ala Trp Lys Arg
 65                  70                  75                  80 atg gag gtc ggg cag cag gcc gta gaa gtc tgg cag ggc ctg gcc ctg     288
Met Glu Val Gly Gln Gln Ala Val Glu Val Trp Gln Gly Leu Ala Leu
                 85                  90                  95 ctg tcg gaa gct gtc ctg cgg ggc cag gcc ctg ttg gtc aac tct tcc     336
Leu Ser Glu Ala Val Leu Arg Gly Gln Ala Leu Leu Val Asn Ser Ser
             100                 105                 110 cag ccg tgg gag ccc ctg cag ctg cat gtg gat aaa gcc gtc agt ggc     384
Gln Pro Trp Glu Pro Leu Gln Leu His Val Asp Lys Ala Val Ser Gly
         115                 120                 125
```

```
ctt cgc agc ctc acc act ctg ctt cgg gct ctg gga gcc cag aag gaa     432
Leu Arg Ser Leu Thr Thr Leu Leu Arg Ala Leu Gly Ala Gln Lys Glu
    130                 135                 140 gcc atc tcc cct cca gat gcg gcc tca gct gct cca ctc cga aca atc     480
Ala Ile Ser Pro Pro Asp Ala Ala Ser Ala Ala Pro Leu Arg Thr Ile
145                 150                 155                 160 act gct gac act ttc cgc aaa ctc ttc cga gtc tac tcc aat ttc ctc     528
Thr Ala Asp Thr Phe Arg Lys Leu Phe Arg Val Tyr Ser Asn Phe Leu
                165                 170                 175 cgg gga aag ctg aag ctg tac aca ggg gag gcc tgc agg aca ggg gac     576
Arg Gly Lys Leu Lys Leu Tyr Thr Gly Glu Ala Cys Arg Thr Gly Asp
            180                 185                 190 aga tga                                                             582
Arg
```

<210> SEQ ID NO 4
<211> LENGTH: 193
<212> TYPE: PRT
<213> ORGANISM: Homo sapiens

<400> SEQUENCE: 4

```
Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

NF-κB ACTIVATION INHIBITORS, AND THEIR PHARMACEUTICAL USES

The present invention has for its object the use of biological inhibitors of NF-κB, in the field of treating cancers, and more particularly malignant hemopathies or solid tumors.

Numerous tumoral cells have developed sophisticated mechanisms permitting them to resist the effect of certain agents used in anti-cancer chemotherapy. One of the countermeasures at present developed by clinicians is the increase of the dosage of these medications, with the result of aggravating the side effects observed in the patients. Thus, for example, most of the leukemias and certain lymphomas are treated by the administration of anthracyclines (daunomycin, dauxorubicin) whose toxicity is manifest in the vital functions (hepatic, cardiac . . . ) (Gauthier, P H, 1987, Gas Med Fr, 94:43–49).

The mechanism of action of the medications has been well studied and has essentially led to the death of tumor cells by apoptosis (Hannum Y A, Blood, 89:1845–1853). To avoid apoptosis, the cells use a category of proteins encoded by genes called multidrug resistant genes (MDR) which permit them to control the intake or outflow of various molecules (Pastan I, Gottesman M M, 1991, Annu Rev Med, 42:277–286). In the case of anti-cancer agents, these are actively evacuated by means of P-glycoprotein (P-gp), produced by the MDR1 gene.

As all genes, the expression of the MDRs is controlled by different nuclear factors. Thus, it has been recently shown that the MDR1 gene has in its regulatory portion binding sites of the NF-κB factor (Zhou G, Kuo M T, 1997, J Biol Chem, 272:15174–15183). This nuclear factor, which moreover plays a considerable role in numerous inflammatory situations (Barnes P J, Karin M, 1997, N Engl J Med, 336:1066–1071) participates in the activation of the MDR1 gene.

Several recent works have established a connection between the inhibition and the activation of NF-κB and the potentialization of apoptosis. In the first reported experiments (Wang C Y et coll., 1996, Science, 272:784–786, Van Antwerp D J et coll., Science, 272:787–789) the authors have validated their data by using genetically manipulated lines to obtain the inhibition or the overexpression of NF-κB activity. Thus, this does not permit their direct use in therapeutic applications.

In another study, the authors have tested the effects of different protease inhibitors preventing the activation of NF-κB (pyrolidine dithiocarbamate, N-tosyl-L-lysl chloromethylcetone, N-acetyl cysteine) on a line of murine macrophages (Mannick E E et coll., 1997, Mediators of Inflammation, 6:225–232). The authors of this article conclude there is a possible connection between NF-κB inhibition and the induction of apoptosis of the inflammatory and immune cells.

Finally, another approach based on inhibition of the inflammatory effects of NF-κB, consists in overexpressing the natural inhibitor of NF-κB, the IκB molecule, by gene therapy (Makarov S S et coll., 1997, Gene Ther, 4:846–852). This technology is also in the state of development because of the complexity and the vectorization necessary for its good operation.

The present invention results from the discovery by the inventors of new effects of the human growth hormone (HGH), also called somatotropin, namely, on the one hand that HGH, and other compounds connected specifically to the transmembrane receptors of class I cytokines, are inhibitors of the activation of NF-κB by a cytotoxic molecule, and, on the other hand, that HGH, and other above-mentioned compounds, permit potentiating the effects of cytotoxic molecules and hence reducing the concentrations of these latter in the field of therapeutic treatments.

First of all, the inventors have observed that the human monocytes respond less to a stimulation by lipopolysaccharides (LPS) when they are cultivated in the presence of exogenous recombinant HGH. The inventors have accordingly concluded that HGH inhibits the activation of NF-κB after stimulation by LPS (Haeffner A et coll., 1997, J Immunol, 158:1310–1314).

Then, the inventors discovered that the human monocytes died after bridging (or engagement) of the surface molecule APO1/CD95/Fas, and have shown that HGH decreases the death mediated through the molecule Fas, by increasing the synthesis of an antiapoptogenic proto-oncogene Bcl-2.

Finally, the inventors have studied the effects of HGH on the -TNF response, because Fas and the p55 receptor of the α-TNF belong to the same family of nerve growth receptors. The human promyeloid leukemic line U937 has been used to carry out this work, because of the insensitivity of human monocytes to the death mediated by α-TNF. Obtaining results opposite those observed with Fas, namely that HGH accelerates the death of these cells mediated by α-TNF, has permitted the inventors to conclude as to the inhibitory effect of HGH on the activation of NF-κB by α-THF, or by other cytotoxic molecules activating NF-κb, such as daunomycin.

Thus, the present invention has for its object to provide a new method for the treatment of cancers, and more particularly malignant hemopathies and solid tumors, offering the advantage of improving both the response of the sick person to certain anti-cancer treatments and also, potentially, the general condition of the sick person.

The invention also has for its object to provide new products for the treatment of said pathologies, having both the advantage of increasing the tumoral cell response to chemotherapy, and to improve the general condition of the patients. The new products of the invention permit decreasing the activation of the NF-κB factor by means of the compound that is used to inhibit the activation of NF-κB, such as the human growth hormone, which is adapted to give rise to the inhibition of the transcription of the MDR genes and hence a reinforcement of the cytotoxic effects of the anti-tumor agents used, with the expected result of decreasing the dosage of these anti-tumor medications.

The invention has for its object the use of compounds inhibiting the activation of NF-κB, for the preparation of medications adapted for the treatment of malign hemopathies and solid tumors.

The invention more particularly has for its object the use of NF-κB inhibitor compounds, for the preparation of medications for the prevention of the appearance or the treatment of phenomena of resistance to cytotoxic molecules used in the field of treatment of the above-mentioned pathologies, these resistance phenomena arising in patients treated with these molecules when these latter are adapted to activate NF-κB.

By compounds inhibiting the activation of NF-κB (also called NF- B inhibitor compounds), there is meant any compound capable of inhibiting in the cells of the organism, the activation of NF-κB caused by the cytotoxic molecules used in the field of treatment of the above-mentioned pathologies, and hence any compound capable of inhibiting the synthesis of proteins (such as P-gp) permitting the cells to eliminate the molecules before they can reach their molecular targets.

The invention relates more particularly to the above-mentioned use of compounds inhibiting the activation of NF-κB, in association with one or several cytotoxic molecules usable in the field of treatment of malign hemopathies or solid tumors, said cytotoxic molecules being adapted to activate the NF-κB factor.

Preferably, the compounds inhibiting the activation of NF-κB used in the scope of the present invention, are compounds binding specifically to the transmembrane receptors of the cytokines of class I in the cells of the organism. Preferably, said compounds are selected from those binding to the above-mentioned receptors whose amino acid sequences of the transmembrane, intracytoplasmic and extramembrane portions have a homology of about 50% to about 70%.

The invention has more particularly for its object the above-mentioned use of compounds inhibiting the activation of NF-κB as defined above, selected from growth hormone, prolactin, erythropoietin, interleukin-4, interleukin-7, G-CSF, GM-CSF, interleukin-3, interleukin-6, of human or other mammal origin.

Preferably, said compounds are selected from growth hormone or erythropoietin.

In this connection the invention has more particularly for its object the above-mentioned use:

of human growth hormone, as obtained by extraction from hypophysary extracts, and purification, or, preferably, of the recombinant human growth hormone as encoded by the nucleotide SEQ ID NO 1, or by any nucleotide sequence derived from this latter by degeneracy of the genetic code and being nevertheless capable of encoding for the human growth hormone whose sequence in amino acids is represented by SEQ ID NO 2, said growth hormone being obtained by transformation of suitable cells with the help of vectors containing a nucleotide sequence such as described above, recovery of the recombinant protein produced by said cells, and purification.

The invention also relates to the above-mentioned use, of any peptide sequence derived by addition and/or deletion and/or substitution of one or several amino acids of the sequence SEQ ID NO 2, and conserving the property of the human growth hormone of inhibiting the activation of NF-κB.

The invention has more particularly for its further object the above-mentioned use of recombinant human erythropoietin such as encoded by the nucleotide sequence SEQ ID NO 3, or by any nucleotide sequence derived from this latter by degeneracy of the genetic code and being nevertheless capable of encoding for human erythropoietin, whose sequence in amino acids is represented by SEQ ID NO 4, said erythropoietin being obtained by transformation of appropriate cells with the aid of vectors containing a nucleotide sequence such as described above, recovery of the recombinant protein produced by said cells, and purification.

The invention also relates to the above-mentioned use, of any peptide sequence derived by addition and/or deletion and/or substitution of one or several amino acids of the sequence SEQ ID NO 4, and preserving the property of human erythropoietin of inhibiting the activation of NF-κB.

The invention has more particularly for its object the above-mentioned use of compounds inhibiting the activation of NF-κB as defined above, for the preparation of a medication administrable by the parenteral route (IM, IV, SC), particularly in the amount of:

about 2 IU/kg of body weight/day in the case of human growth hormone, of about 150 IU/kg of body weight/day in the case of human erythropoietin.

Among the cytotoxic molecules adapted to activate the NF-κB factor used in association with said compounds inhibiting the activation of NF-κB within the scope of the present invention, can be cited:

the cytokines, the anthracyclines, of which may be mentioned daunomycin, and dauxorubicin, the vinca-alkaloids, such as vinblastine and vincristin, paclitaxel (or Taxol, DCI).

Preferably, the dosage of the cytotoxic molecules used in association with said compounds is about 2 to about 5 times less than the dosage of these same molecules used alone in the scope of the treatment of malignant hemopathies and solid tumors.

By way of illustration:

the usual daily dose of daunomycin or dauxorubicin being from 40 to 60 mg/m$^2$, the dosage of these latter in the scope of the present invention is about 5 to 30 mg/m$^2$, the usual daily dosage of vinblastine being from 5 to 7 mg/m$^2$, the dosage of this latter in the scope of the present invention is about 1 to 4 mg/m$^2$, the usual daily dosage of vincristin being from 1 to 2 mg/m$^2$, the dosage of this latter in the scope of the present invention is about 0.1 to 1 mg/m$^2$, the usual daily dosage of taxol being about 75 mg/m$^2$, the dosage of this latter in the scope of the present invention is about 15 to 35 mg/m$^2$.

Among the cancers adapted to be treated in the scope of the present invention, can be cited principally:

malignant hemopathies such as leukemias, lymphomas, solid tumors such as those of the ovary or the breast.

The invention also has for its object any product containing:

a compound inhibiting the activity of NF-κB such as described above, and more particularly a compound binding specifically to the transmembrane receptors of the class I cytokines as defined above, and a cytotoxic molecule adapted to activate the NF-κB factor, as a combined preparation for simultaneous use, separate or prolonged over time, for the treatment of malignant hemopathies and solid tumors.

The invention also has for its object any product as defined above, as a combined preparation for simultaneous use, separate or over time, for the prevention of the appearance, or for the treatment, of phenomena of resistance to cytotoxic molecules used in the scope of treatment of the above-mentioned pathologies, appearing in patients treated with molecules when these latter are adapted to activate NF-κB.

The invention relates more particularly to any product as defined above, characterized in that it comprises as a compound inhibiting the activation of NF-κB, growth hormone, prolactin, erythropoietin, interleukin-4, interleukin-7, G-CSF, GM-CSF, interleukin-3, interleukin-6.

Products particularly preferred in the scope of the present invention, are those comprising as a compound inhibiting the activation of NF-κB, growth hormone or erythropoietin.

The invention has more particularly for its object any product as defined above, characterized in that it comprises:

human growth hormone obtained by extraction from hypophysary extracts, and purification, or, preferably, recombinant human growth hormone as described above, encoded by the nucleotide sequence SEQ ID NO 1, or by any nucleotide sequence derived from this latter by degeneracy of the genetic code and being nevertheless capable of encoding for the human growth hormone whose sequence of amino acids is represented by SEQ ID NO 2, or any peptide sequence derived by addition and/or deletion and/or substitution of one or several amino acids of the sequence SEQ ID NO 2, and preserving the property of human growth hormone to inhibit the activation of NF-κB.

The invention also has for its object any product as defined above, characterized in that it comprises recombinant human erythropoietin such as described above, encoded by the nucleotide sequence SEQ ID NO 3, or by any nucleotide sequence derived from this latter by degeneracy of the genetic code and being nevertheless capable of encoding for human erythzopoietin whose sequence in amino acids is represented by SEQ ID NO 4, or any peptide sequence derived by addition and/or deletion and/or substitution of one or several amino acids of the sequence SEQ ID NO 4, and preserving the property of human erythropoietin to inhibit the activation of NF-κB.

The invention also relates to any product as described above, characterized in that it comprises as cytotoxic molecule adapted to activate the NF-κB factor, any molecule selected from the following:
  cytokines,
  anthracyclines, such as daunomycin or dauxorubicin,
  vinca-alkaloids, such as vinblastine and vincristine,
  paclitaxel (or Taxol, DCI).

Products such as those defined above that are preferred in the scope of the present invention, are characterized in that they contain:
  growth hormone and daunomycin or dauxorubicin, in proportions such that their daily dosage is about 2 IU/kg of growth hormone for about 5 to 30 mg/m² of daunomycin or dauxorubicin,
  growth hormone and vinblastine, in proportions such that their daily dosage is about 2 IU/kg of growth hormone for about 1 to 4 mg/m² of vinblastine,
  growth hormone and vincristine, in proportions such that their daily dosage is about 2 IU/kg of growth hormone for about 0.1 to 1 mg/m² of vincristine,
  growth hormone and taxol, in proportions such that their daily dosage is about 2 IU/kg of growth hormone for about 15 to 35 mg/m² of taxol,
  erythropoietin and daunomycin or dauxorubicin, in proportions such that their daily dosage is about 150 IU/kg of erythropoietin for about 5 to 3 mg/m² of daunomycin or dauxorubicin,
  erythropoietin and vinblastine, in proportions such that their daily dosage is about 150 IU/kg of erythropoietin for about 1 to 4 mg/m² of vinblastine,
  erythropoietin and vincristine, in proportions such that their daily dosage is about 150 IU/kg of erythropoietin for about 0.1 to 1 mg/m² of vincristine,
  erythropoietin and taxol, in proportions such that their daily dosage is about 150 IU/kg of erythropoietin for about 15 to 35 mg/m² of taxol.

The invention is illustrated with the help of the following detailed description of the in vitro effect of growth hormone and erythropoietin on tumoral cell lines.

1) EXAMPLE NO. 1

A selection gene (neomycin resistant, Neo$^R$) and the gene encoding for human growth hormone (HGH) have been co-transfected in the human promyeloid leukemic line U937. By comparing the transfected line U937-HGH (which produces in a constituent fashion HGH at physiologic doses), either to the parent line U937, or to a line transfected with Neo$^R$ alone, there are observed by different methodological approaches, that the U937-HGH line dies more under the effect of the tumor necrosis factor (-TNF). This cytokine secreted by different types of immune cells has in an anti-tumor activity (Harakana, K et al., 1984, Int J Cancer, 34:263–267) and is capable of promoting the activation of NF-κB (Baeuerle P A, Henkel T, 1994, Ann Rev Immunol, 12:141–179).

The U937-HGH cells and the U937-Neo control cells have been cultured for 48 hours in the presence of increasing concentrations of recombinant -TNF. As a result of this culture, the washed cells have been incubated in the presence of propidium iodide which is incorporated in the DNA of the dead cells. These cells are analyzed by flowing cytometry.

Figure 1:
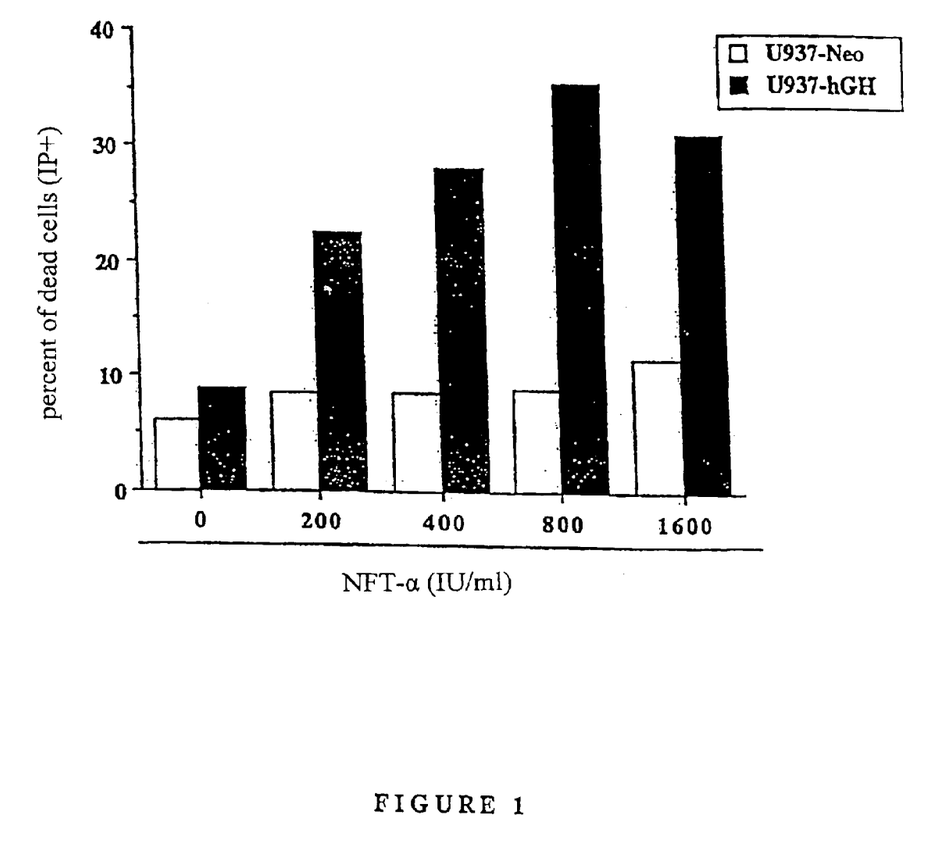
FIG. 1: The effect of growth hormone on the mortality of cells exposed to -TNF: the percentage of the dead cells (IP+) is indicated on the ordinate, the white colonies corresponding to the cells of the strain U937-Neo, the black colonies corresponding to the cells of the strain U937-hGH; the concentrations of NFT- are indicated on the abscissa in IU/ml.

FIG. 1 shows the increase of the incorporation of propidium iodide as a function of increasing doses of -TNF expressed in international units (IU). For the U937 cells (the mother line having served to obtain the U937-HGH lines), with increase of the concentration of -TNF, there is observed a slight increase of the percentage of fluorescent cells (thus dead) due to the incorporation of propidium iodide (red fluorescence). This figure shows on the other hand clearly the fact that these values are much higher for the U937-HGH line, as a function of increasing doses of -TNF added to the same culture.

It is thus demonstrated that the presence in the cellular cultures of HGH produced by the U937 lines transfected with the HGH gene, increases their susceptibility to the induction of death mediated by -TNF.

2) EXAMPLE NO. 2

Having reported in a previous study that HGH could intervene in the inhibition of the activation of NF-κB mediated by lipopolysaccharides (Haeffner A et coll., 1997, J Immunol, 158:1310–1314), the inventors have studied the status of NF-κB during stimulation of the different lines by -TNF.

Figure 2:
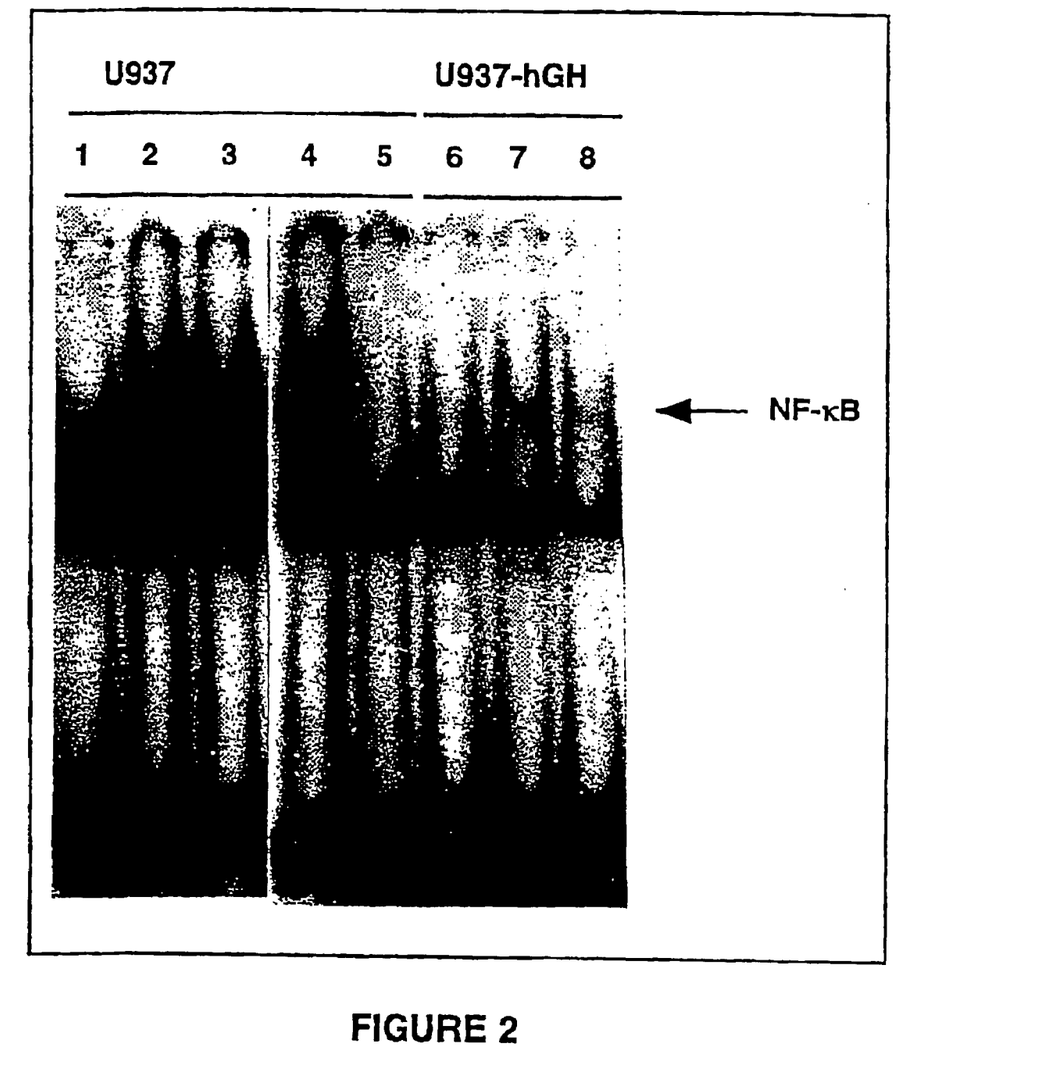
FIG. 2: The effect of growth hormone on the translocation of NF-κB; column 1 corresponds to the control cells U937, column 2 corresponds to the U937 cells treated with -TNF+ cycloheximide, column 3 corresponds to the U937 cells treated with -TNF, column 4 corresponds to the U937 cells treated with -TNF+a mutant NF-κB probe, column 5 corresponds to the U937 cells treated with -TNF +a homologous NF-κB probe, column 6 corresponds to the control cells U937-HGH, column 7 corresponds to the U937-HGH cells treated with -TNF+cycloheximide, column 8 corresponds to the U937-HGH cells treated with -TNF; the presence of NF-κB is indicated by an arrow.

FIG. 2 shows the result of an analysis by gel delay. On this gel were deposited nuclear extracts from the U937-HGH and U937 cells (the mother line having served for obtaining the U937-HGH lines) subjected to different inductors including -TNF or -TNF and cycloheximide (inhibitor of protein synthesis). This experiment indicates clearly that the presence of NF-κB in the nuclei of the U937-HGH cells, is decreased relative to the control cells.

The presence of NF-κB is seen in lines 4 and 5, which represent the migration of the nuclear extracts of U937 cells stimulated by -TNF, and pre-incubated, either with a cold probe muted NF-κB which does not displace the signal (line 4), or with a cold probe NF-κB homolog which inhibits the signal (line 5).

Figure 3:
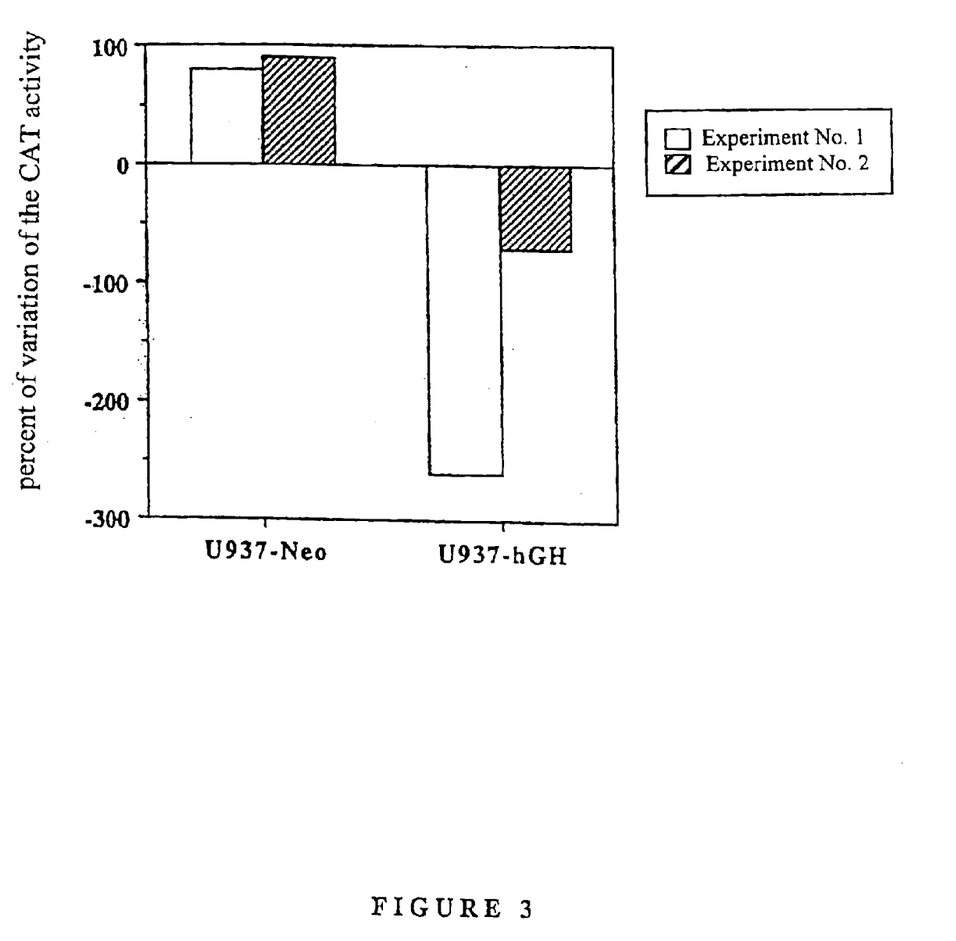
FIG. 3: Effect of growth hormone on the reporter activity CAT; the percentage of variation of CAT activity is indicated on the abscissa; the two left columns show the two experiments carried out on U937-Neo cells, and the two right columns represent the two independent experiments carried out on U937-HGH cells.

FIG. 3 shows the result of an enzyme immunoassay (ELISA) carried out with the lysate of U937-HGH and U937-Neo cells transfected in a transitory manner with a plasmid containing NF-κB sequences in the promotor of the reporter gene encoding for chloramphenicol-acetyl-transferase (CAT) (Chiao P et coll., 1994, Proc Natl Acad Sci USA, 91:28–32).

The cells are transfected by electroporation then incubated with -TNF. At the end of culturing, the cells are lysated and the activated CAT is measured by an commercial ELISA (Boehringer-Mannheim), according to the directions of the supplier.

The figure shows that the CAT activity, reflected by the presence of NF-κB, is decreased in the U937-HGH cells relative to the control cells, after stimulation by -TNF.

The results shown in FIGS. 2 and 3 therefore show by two different methodological approaches, that the synthesis of NF-κB is decreased in U937-HGH relative to the control line.

3) EXAMPLE NO. 3

The use of -TNF being very difficult in human clinical work because of the adverse side effects, the inventors are interested in daunomycin. This anthracyclin used in anti-cancer therapy under the name of Cerubidine acts by insertion in the cellular DNA sequences, thus disturbing the cellular function. Like -TNF (Baeuerle P A, Henkel T, 1994, Ann Rev Immunol, 12:141–179), daunomycin activates NF-κB (Das K C, White C W, 1997, J Biol Chem, 272:14914–14920).

Figure 4:
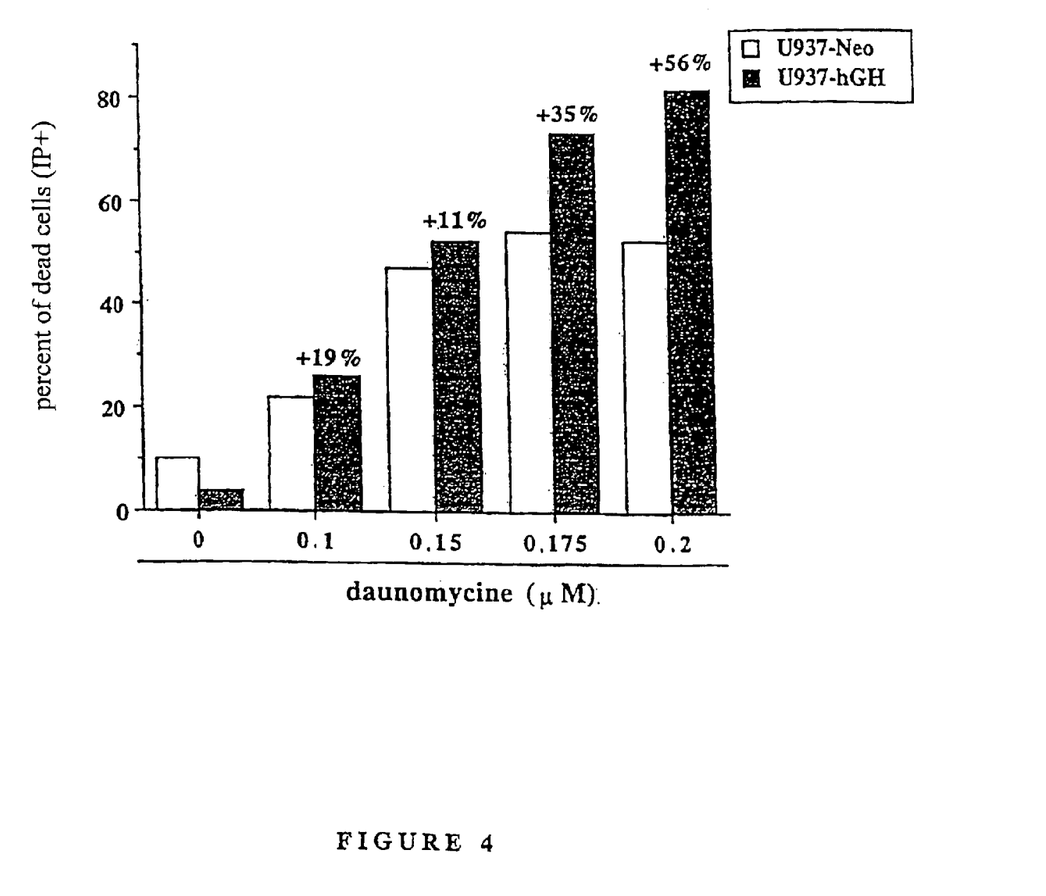
FIG. 4: Effect of growth hormone on apoptosis induced by daunomycin; the percentage of the dead cells (IP+) is indicated on the ordinate, the white columns corresponding to the cells of the strain U937-Neo, the black columns corresponding to the cells of the strain U937-HGH; the indicated percentages show the increase of mortality of the cells; the concentrations of daunomycin are indicated on the abscissa in μM.

FIG. 4 indicates that the U937-HGH line is also more sensitive than the control line to the mediated death by daunomycin.

4) EXAMPLE 4

To test the possibility of using the object of the present invention on non-lymphoid tumors, the inventors have used HGH to try to invert the "adriamycine resistant" phenotype of cells isolated from a human ovarian adenocartcinoma IGROV/ADR (Bénard J et coll., 1985, Cancer Res, 45:4970–4979).

Figure 5:
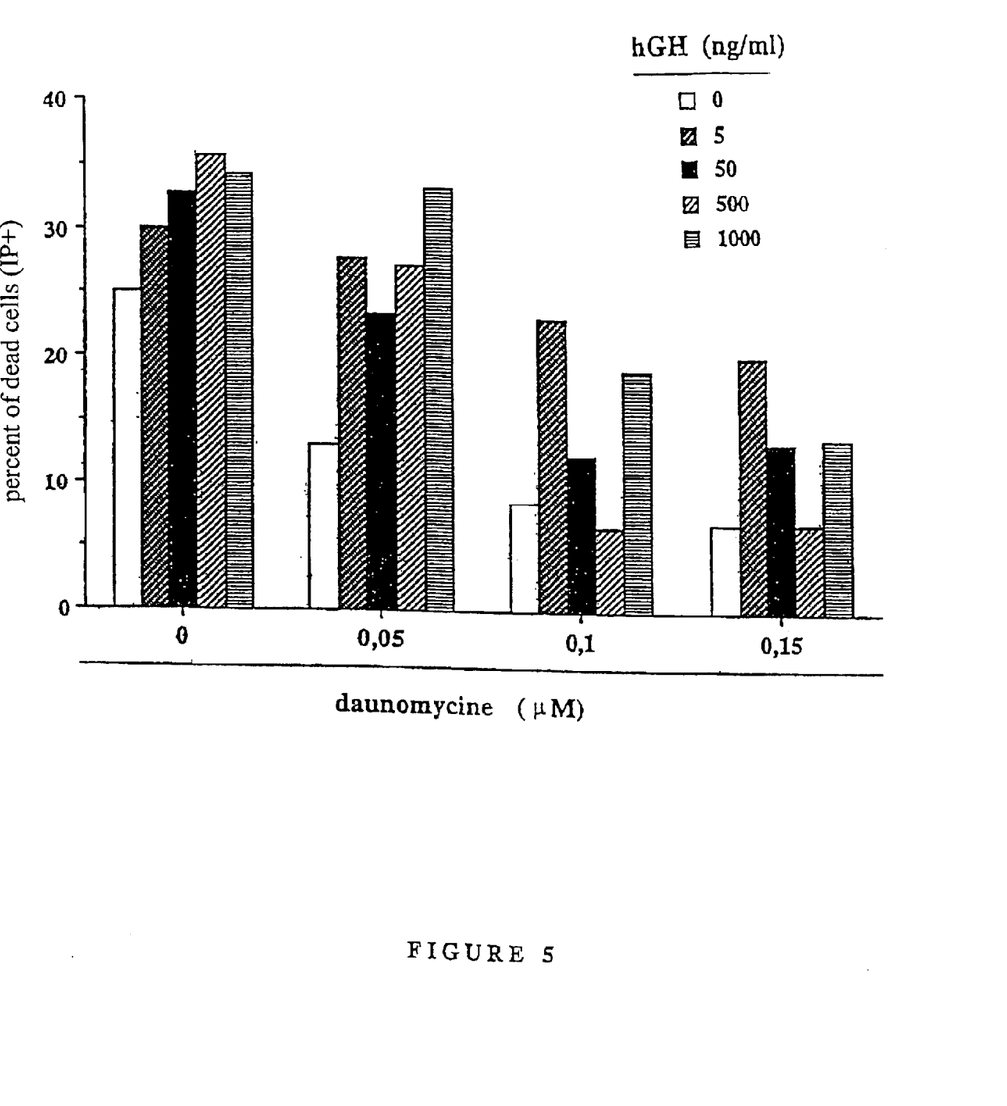
FIG. 5: Effect of growth hormone on the apoptosis of the IGROV/ADR line, induced by daunomycin; the percentage of dead cells (IP+) is indicated on the ordinate, and different columns corresponding to the different concentrations of HGH used (0, 5, 50, 500, 1000 ng/ml); the concentrations of daunomycin are indicated on the abscissa in μM.

As shown by FIG. 5, these cells are insensitive to the toxic effect of the daunomycin added to the culture (HGH groups 0 ng/ml). The addition of recombinant HGH (Saizen$^R$, Serono laboratory) renders these cells sensitive to daunomycin, with a maximum effect observed for the lowest dose of HGH used here, namely 5 ml/ml.

These result proves on the one hand that the results of aggravated mortality can be obtained as well with recombinant exogenous HGH as with the transfected lines mentioned above, and that on the other hand, the present invention can be applied to non-lymphoid solid tumors.

5) EXAMPLE NO. 5

Erythropoietin (EPO), another molecule than HGH belonging to the same family of cytokines of class I, has been tested on human renal carcinoma cells (RCC) HIEG.

Figure 6:
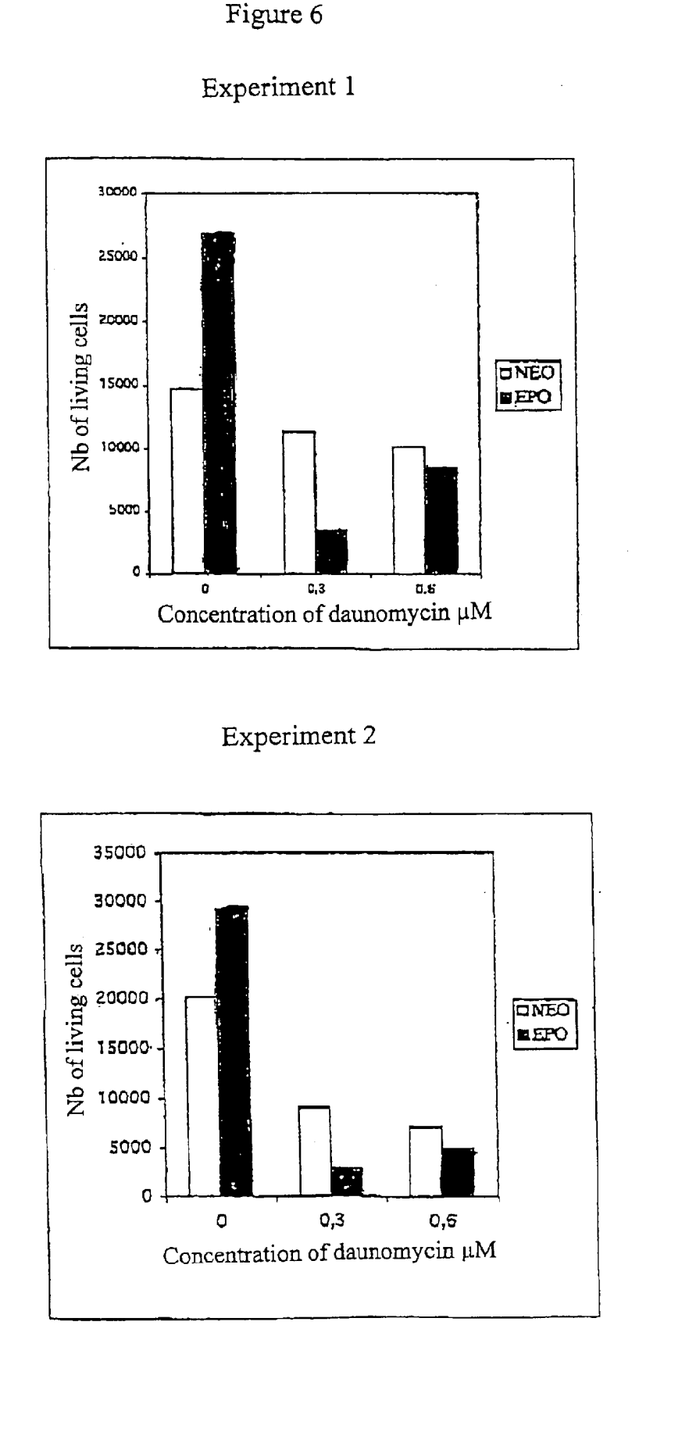
FIG. 6: Effect of erythropoietin on the apoptosis of the human renal carcinoma line HIEG, induced by daunomycin: for each of the experiments 1 and 2, the number of living cells is indicated on the ordinate, the white columns correspond to the RCC-Neo cells, the black columns correspond to the RCC-EPO cells; the concentrations of daunomycin are indicated on the abscissa in μM.

$4.10^4$ RCC cells have been transfected in a transitory manner with the help of an Effecten$^R$ kit, or with 3 μg of plasmid carrying the gene encoding for EPO (RCC-EPO cells), or with 3 μg of a plasmid coding for the resistance to neomycin (RCC-Neo cells) as the negative control. After 48 hours, the RCC were combined with daunomycin at two different concentrations: 0.3 and 0.6 μM. The number of surviving cells was measured 48 hours later by flow cytometry (FIG. 6).

The results of Experiment 1 expressed in numbers of living cells are as follows:

|  | RCC-Neo | RCC-EPO |
|---|---|---|
| daunomycin 0 μM | 14745 | 26911 |
| daunomycin 0.3 μM | 11382 | 3487 |
| daunomycin 0.6 μM | 10179 | 8551 |

The results of Experiment 2 expressed in numbers of living cells are as follows:

|  | RCC-Neo | RCC-EPO |
|---|---|---|
| daunomycin 0 μM | 20150 | 29102 |
| daunomycin 0.3 μM | 8891 | 2693 |
| daunomycin 0.6 μM | 7001 | 4739 |

The results show that in the two different experiments (Experiments 1 and 2), the conjoint presence of daunomycin and EPO aggravates substantially the cellular mortality, with a more marked effect for the lower dose of daunomycin used.

What is claimed is:

1. A method for treating a patient with a pathology selected from the group consisting of malignant hemopathies and solid tumors, wherein said patient is resistant to, or at risk of developing a resistance to a NF-κB-activating cytotoxic molecule which is administered to said patient in the scope of the treatment of said pathology, comprising administering to said patient an effective amount of human growth hormone comprising SEQ ID NO: 2.

2. The method according to claim 1, wherein the human growth hormone is encoded by SEQ ID NO: 1.

3. The method according to claim 1, wherein the cytotoxic molecule is an anthracycline.

4. The method according to claim 1, wherein the cytotoxic molecule is paclitaxel.

5. The method according to claim 1, wherein the cytotoxic molecule is an anthracycline and the dosage of said anthracycline administered with said growth hormone is about 2 to about 5 times less than the dosage of said anthracycline administer alone in the scope of the treatment of said pathology.

6. The method according to claim 1, wherein the cytotoxic molecule is paclitaxel and the dosage of paclitaxel administer with said growth hormone is about 2 to about 5 times less than the dosage of paclitaxel administered alone in the scope of the treatment of said pathology.

* * * * *